United States Patent [19]

Elliott et al.

[11] 4,246,257
[45] Jan. 20, 1981

[54] COSMETIC DEGREASING AND MATTING COMPOSITION

[75] Inventors: Thomas J. Elliott, London; David Ford, Isleworth, both of England

[73] Assignee: Beecham Group Limited, England

[21] Appl. No.: 9,223

[22] Filed: Feb. 2, 1979

Related U.S. Application Data

[63] Continuation of Ser. No. 800,026, May 24, 1977, abandoned.

[30] Foreign Application Priority Data

Dec. 9, 1976 [GB] United Kingdom ............... 51372/76

[51] Int. Cl.$^2$ .................... A61K 7/00; A61K 7/48; A61K 31/74
[52] U.S. Cl. ........................ 424/78; 424/69; 424/79; 424/81; 424/83; 424/358
[58] Field of Search ............ 424/69, 78, 79, 81, 424/83, 358

[56] References Cited

U.S. PATENT DOCUMENTS

| 3,196,079 | 7/1965 | Blaustein | 424/69 |
|---|---|---|---|
| 3,823,114 | 7/1974 | Albarino | 260/45.9 R |
| 3,846,550 | 11/1974 | Akrongold | 424/69 |
| 3,862,310 | 1/1975 | Quasius | 424/65 X |
| 4,151,272 | 4/1979 | Geary | 424/67 X |

FOREIGN PATENT DOCUMENTS

| 2021677 | 12/1971 | Fed. Rep. of Germany | 424/78 |
|---|---|---|---|
| 926862 | 5/1963 | United Kingdom | 424/63 |
| 1141994 | 2/1969 | United Kingdom | 424/69 |
| 552083 | 3/1977 | U.S.S.R. | 424/79 |

OTHER PUBLICATIONS

Weber, Chem. Abs., vol. 76, 1972, Ab. No. 101564m.

*Primary Examiner*—Anna P. Fagelson
*Attorney, Agent, or Firm*—Jacobs & Jacobs

[57] ABSTRACT

Skin treatment product for greasy or oily skin comprising an unpigmented oil-in-water or water-in-oil emulsion having dispersed therein 3 to 10% by weight of spherical polymer or copolymer particles having an average size of 5 to 15 microns. The polymer or copolymer particles are cross-linked polystyrene, polymethylmethacrylate or polyethylene microspheres. The oil of the emulsion is a volatile organic liquid in the amount of 1 to 30% of the weight of the emulsion and may be a silicone or silicon glycol.

6 Claims, No Drawings

COSMETIC DEGREASING AND MATTING COMPOSITION

This is a continuation of Ser. No. 800,026, filed May 24, 1977, now abandoned.

This invention relates to a composition of cream-like or lotion consistency containing tiny polymer particles. The composition, when applied to the skin, imparts a matte effect.

Many people have what is commonly known as a greasy or oily skin, and this is regarded as cosmetically unattractive. Consequently, skin treatment products are available which either assist in removing excess sebum from the surface of the skin or mask the sheen on the skin. The former products may take the form of cleansing lotions or creams, or tissues, impregnated with a mild solvent such as alcohol/water. These products are only temporarily effective since sebum production is continuous.

Attempts have been made in the past to incorporate absorbent solid materials such as talc into the cleansing products to absorb the sebum. These have not been successful because the residual talc is usually visible on the skin.

We have found that emulsions with water as the continuous or discontinuous main phase and with volatile, cosmetically acceptable organic solvents as the discontinuous or continuous secondary phase and furthermore containing small amounts of tiny spherical polymer particles, are particularly useful as skin "matting" treatments. Accordingly, the present invention provides a skin treatment product comprising an unpigmented oil-in-water (or water-in-oil) emulsion wherein the oil is a cosmetically acceptable volatile organic liquid present in an amount of from 1 to 30% by weight of the emulsion, said emulsion having dispersed therein from 3 to 10% by weight of substantially spherical polymer or copolymer particles having an average particle size in the range 5 to 15 microns.

Cosmetically acceptable volatile organic liquids are those which are safe to use on the skin and which evaporate from the skin after a relatively short period of contact, e.g. after from 1 to 10 minutes. Examples include certain silicones and silicone glycols as well as certain hydrocarbons.

Examples of volatile organic liquids include:
A mixture of aliphatic isoparaffins with boiling range 180°-210° C. (Shellsol T),
Cyclic dimethyl silicone with boiling point approximately 170° C. (Silicone 7207),
Cyclic dimethyl silicone with boiling range 190°-210° C. (Silicone 7158).

Usually the product will contain a perfume.

Usually the product will contain from 3 to 5% by weight of the polymer or copolymer particles.

Preferably the polymer or copolymer particles shall have an average size of from 5 to 7 microns.

Preferably, substantially none of the polymer or copolymer particles should exceed about 50 microns, and best results are achieved when there are substantially no paticles of a size greater than 15 microns.

The polymer or copolymer particles should preferably not swell to any great extent in water or the organic liquid used in the product. Within this limitation cross-linked polystyrene or polymethylmethacrylate microspheres would be suitable. However, the preferred polymer is polyethylene.

The following are Examples of the formulae of certain products according to the invention:

| FORMULA | % w/w |
|---|---|
| Moisturising Lotion oil-in-water Emulsion | |
| Stearic acid | 3.00 |
| Propylene glycol monostearate (S/E) | 1.00 |
| Polawax | 1.00 |
| Volatile organic liquid (Shellsol T) | 5.00 |
| Decyl myristate | 5.00 |
| Triethanolamine | 1.00 |
| *Polymist B-6 | 5.00 |
| Preservatives | qs |
| Perfume | qs |
| Distilled water | 79.00 |
| | 100.00 |
| Night Cream water-in-oil Emulsion | |
| Arlacel 186 (emulsifier) | 1.50 |
| Sorbitol (70%) | 9.00 |
| Ceresin wax | 2.00 |
| Beeswax | 2.00 |
| Cosmolloid wax 85 (microcrystalline hydrocarbon wax) | 2.00 |
| Volatile organic liquid (Silicone 7207) | 15.00 |
| *Polymist B-6 | 5.00 |
| Preservatives | qs |
| Perfume | qs |
| Distilled water | 63.50 |
| | 100.00 |

*Polymist is a Trade Mark of Allied Chemicals; Station House, Stamford New Road, Altrincham, Cheshire WA16 1 EP, England.

Polymist B-6 is high density (0.96 gm/cc by ASTM D-1505) polyethylene microspheres having an average particle size of 6µ a particle size range of from 2–12µ with less than 2% of the particles larger than 10 µ.

We claim:

1. A skin degreasing and matting product comprising from 3 to 10% by weight of composition of substantially spherical particles of a polymer or copolymer selected from the group consisting of polyethylene, polystyrene and polymethylmethacrylate, said particles having an average size of from 5 to 15 microns and being dispersed in an unpigmented aqueous emulsion of a volatile, cosmetically acceptable oil in an amount of from 1 to 30% by weight of said emulsion.

2. The product of claim 1 containing from 3 to 5% by weight of the polymer or copolymer particles.

3. The product of claim 1 wherein the polymer or copolymer particles have an average size of from 5 to 7 microns.

4. The product of claim 1 wherein substantially none of the polymer or copolymer particles exceed about 15 microns.

5. The product of claim 1 wherein the volatile organic oil is a silicone or silicone glycol.

6. A skin degreasing and matting product comprising from 3 to 10% by weight of the composition of non-swelling polyethylene microspheres of average particle size of 5 to 7 microns, with substantially no particles greater than 15 microns, dispersed in an aqueous emulsion of a volatile liquid silicone or silicone glycol in an amount of 1 to 30% by weight of emulsion.

* * * * *